US008199685B2

(12) United States Patent
Hwang

(10) Patent No.: US 8,199,685 B2
(45) Date of Patent: Jun. 12, 2012

(54) PROCESSING OF MEDICAL SIGNALS

(75) Inventor: Juinjet Hwang, Mercer Island, WA (US)

(73) Assignee: SonoSite, Inc., Bothell, WA (US)

(*) Notice: Subject to any disclaimer, the term of this patent is extended or adjusted under 35 U.S.C. 154(b) by 2064 days.

(21) Appl. No.: 10/847,643

(22) Filed: May 17, 2004

(65) Prior Publication Data
US 2005/0265267 A1 Dec. 1, 2005

(51) Int. Cl.
*H04B 7/00* (2006.01)

(52) U.S. Cl. ............. 370/310.2; 370/310; 370/338; 455/41.2; 455/41.3; 455/418; 455/419; 455/420; 455/90.1; 455/3.06; 455/556.1; 455/557; 600/300; 600/407; 600/437; 600/459; 378/102; 378/198; 705/2; 705/3

(58) Field of Classification Search ............. 370/310, 370/310.2, 328, 338; 455/41.2, 41.3, 3.06, 455/90.1, 556.1, 418–420, 66.1; 600/300, 600/407, 437–440, 459; 705/2, 3; 378/102, 378/198; 358/1.15; 367/168
See application file for complete search history.

(56) References Cited

U.S. PATENT DOCUMENTS

| 5,295,485 | A | 3/1994 | Shinomura et al. |
| 5,360,005 | A | 11/1994 | Wilk |
| 5,500,517 | A | 3/1996 | Cagliostro |
| 5,590,658 | A | 1/1997 | Chiang et al. |
| 5,722,417 | A | 3/1998 | Garbe |
| 5,772,412 | A | 6/1998 | Zytynski |
| 5,795,297 | A | 8/1998 | Daigle |
| 5,882,300 | A | 3/1999 | Malinouskas et al. |
| 5,930,719 | A | 7/1999 | Babitch et al. |
| 5,971,923 | A | 10/1999 | Finger |
| 6,113,547 | A | 9/2000 | Catallo et al. |
| 6,120,447 | A * | 9/2000 | Mullen .......... 600/437 |
| 6,126,608 | A * | 10/2000 | Kemme et al. ........ 600/459 |
| 6,142,946 | A | 11/2000 | Hwang et al. |
| 6,238,344 | B1 | 5/2001 | Gamelsky et al. |
| 6,241,673 | B1 | 6/2001 | Williams |
| 6,363,033 | B1 * | 3/2002 | Cole et al. ............ 367/138 |
| 6,440,072 | B1 | 8/2002 | Schuman et al. |
| 6,472,651 | B1 | 10/2002 | Ukai |
| 6,475,146 | B1 * | 11/2002 | Frelburger et al. ...... 600/437 |
| 6,478,740 | B2 | 11/2002 | Souney et al. |
| 6,481,887 | B1 | 11/2002 | Mirabella |
| 6,569,097 | B1 * | 5/2003 | McMorrow et al. ....... 600/437 |

(Continued)

FOREIGN PATENT DOCUMENTS

DE 101 12 409 A1 9/2002

(Continued)

OTHER PUBLICATIONS

Partial International Search Report issued for PCT/US2005/017002 dated Feb. 1, 2006.

(Continued)

*Primary Examiner* — Stephen M D'Agosta
(74) *Attorney, Agent, or Firm* — Fenwick & West LLP

(57) ABSTRACT

Systems and methods in which real-time ubiquitous imaging is feasible in local areas, such as inside a clinic, hospital room or doctor office are shown. This is achieved by designing a wireless network having a central processing server with, for example, distributed broadband acquisition and video bus capability. Remote access is possible using store-and-forward image transfer over a wide area network. With these capabilities, a physician can use a handheld transducer (such as an ultrasound transducer) as a basic tool to facilitate diagnostic decisions similar to the way a stethoscope is used today.

3 Claims, 3 Drawing Sheets

U.S. PATENT DOCUMENTS

| | | |
|---|---|---|
| 6,625,252 B2 | 9/2003 | Mirabella |
| 6,659,947 B1 * | 12/2003 | Carter et al. .................. 600/300 |
| 6,705,990 B1 | 3/2004 | Gallant et al. |
| 6,780,154 B2 | 8/2004 | Hunt et al. |
| 2002/0016545 A1 | 2/2002 | Quistgaard et al. |
| 2002/0040186 A1 | 4/2002 | Souney et al. |
| 2002/0072933 A1 | 6/2002 | Vonk et al. |
| 2003/0073894 A1 | 4/2003 | Chiang et al. |
| 2004/0030585 A1 | 2/2004 | Sariel |
| 2004/0061889 A1 * | 4/2004 | Wood et al. .................. 358/1.15 |

FOREIGN PATENT DOCUMENTS

| | | |
|---|---|---|
| JP | 2002152314 | 5/2002 |
| JP | 2002200077 A | 7/2002 |
| JP | 2003299647 A | 10/2003 |
| WO | 0066001 A1 | 11/2000 |
| WO | WO 00/70366 | 11/2000 |
| WO | 0079300 A1 | 12/2000 |
| WO | 0207586 A2 | 1/2002 |

OTHER PUBLICATIONS

European Search Report issued for EP 05749899.0 dated Aug. 14, 2007.

Examination Report issued Feb. 22, 2010 in European Application No. 05749899.0, 4 pages.

* cited by examiner

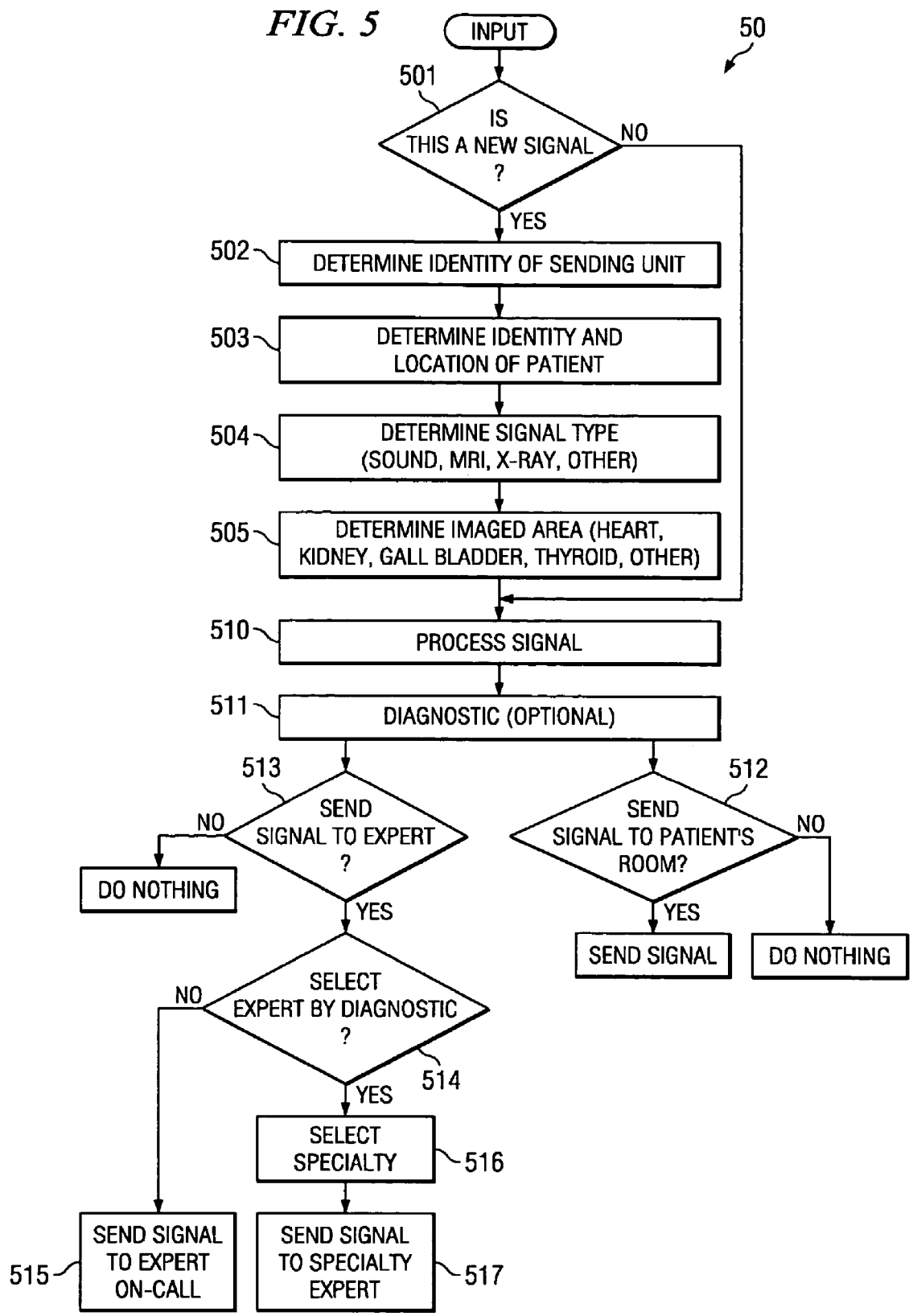

PROCESSING OF MEDICAL SIGNALS

CROSS REFERENCE TO RELATED APPLICATIONS AND PATENTS

The present application is related to co-pending, and commonly-assigned U.S. patent application Ser. No. 10/821,123, entitled "Systems And Methods Providing ASICS For Use In Multiple Applications," filed Apr. 8, 2004 and U.S. patent application Ser. No. 10/821,198, entitled "System And Method For Enhancing Gray Scale Output On A Color Display," filed Apr. 8, 2004; the disclosures of which are all hereby incorporated herein by reference herein.

TECHNICAL FIELD

The embodiments of this disclosure are directed to medical diagnostic and/or treatment systems and more particularly to systems and methods for the ubiquitous processing of medical signals originating from medical equipment at diverse locations.

BACKGROUND OF THE INVENTION

Similar to the development of PCs in computing and cellular telephones in mobile communication, system miniaturization can bring high performance to medical diagnostic equipment. Even sophisticated imaging devices, such as obtained by portable ultrasound transducers, are available at the point-of-care.

For ubiquitous imaging, it is necessary that the imaging system transducer be easily moved from patient to patient and thus it must have a high degree of portability. Such systems however, typically have limited network connectivity and storage and generally lack the capability of accessing patient files or other relevant medical information that reside within a hospital information system.

As any new technology or application evolves, new operational issues and demands from users arise. Some of these issues are: image quality, user interface, display size, battery power, packaging, system size and weight, transducer size and weight, image analysis and connectivity. When images are involved high performance (i.e., sharp images, detailed analysis, etc.) is demanded. The requirement of high performance, however, typically increases the complexity of system design and is generally in conflict with the requirement of smaller system size necessary for mobility.

One way to reduce the system size and weight is through elimination of system features and imaging functions. However, by doing so this will also result in possible undesirable reduction of clinically efficacy.

BRIEF SUMMARY OF THE INVENTION

The present invention is directed to a system and method in which real-time ubiquitous imaging is feasible in local areas, such as inside a clinic, hospital room or doctor office. This is achieved by designing a wireless network having a central processing server with, for example, distributed broadband acquisition and video bus capability. Remote access is possible using store-and-forward image transfer over a wide area network. With these capabilities, a physician can use a handheld transducer (such as an ultrasound transducer) as a basic tool to facilitate diagnostic decisions similar to the way a stethoscope is used today.

In one embodiment, a handheld ultrasound imaging system is constructed similar in size to a cellular handset. The imaging system has wireless connectivity, using, for example, a low cost CMOS process for implementing imaging functions with signal processors. This enables medically relevant information to be accessible by the handheld ultrasound device and also allows images acquired from the handheld device to be transferred and retrieved from a number of locations while the signals are processed from a location common to all of those locations.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 5 shows one embodiment of a flow chart of system operation.

DETAILED DESCRIPTION OF THE INVENTION

Figure 1:
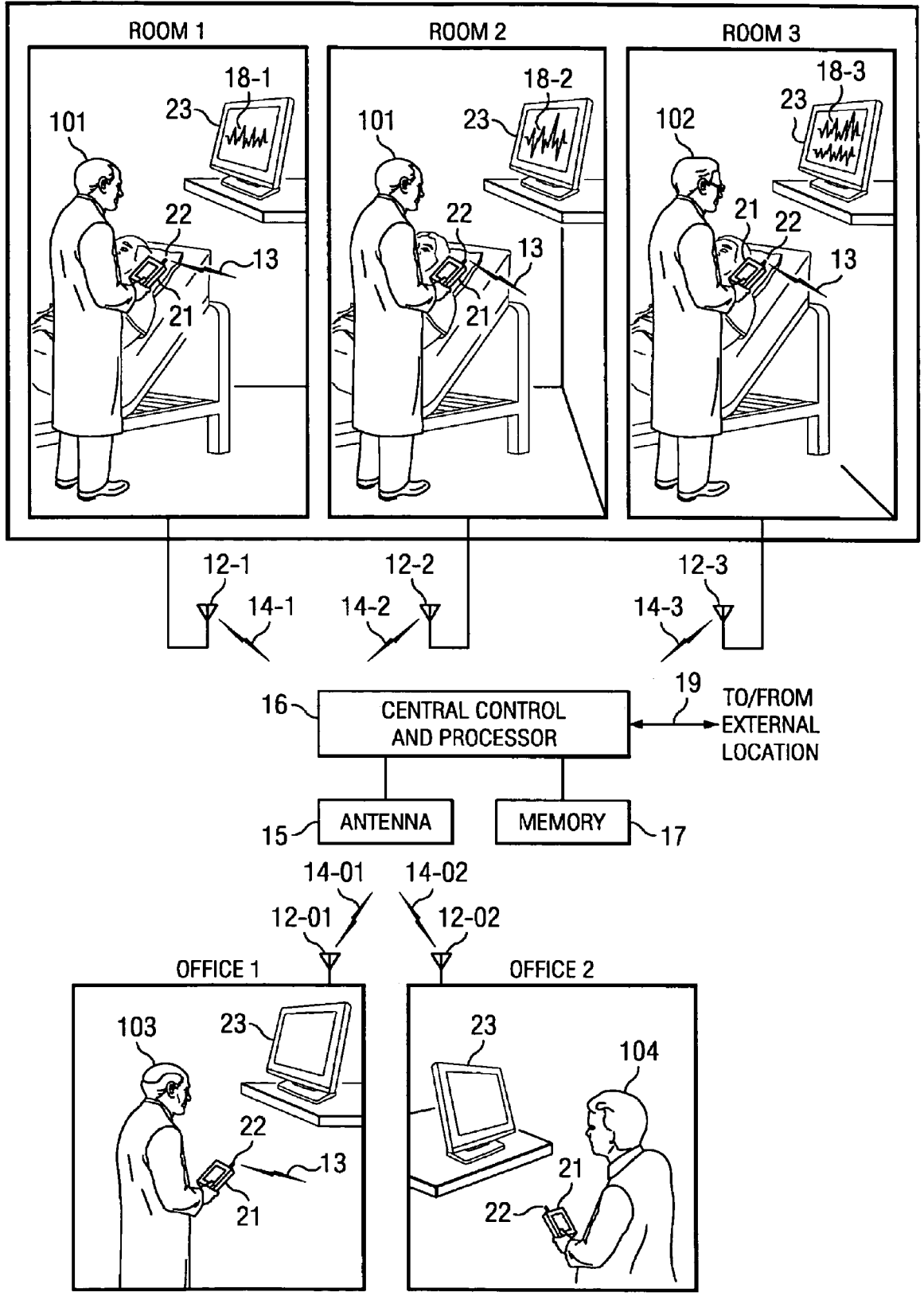
FIG. 1 shows a block diagram of one embodiment of a multi-room system where processing of data from many rooms is performed centrally.

FIG. 1 shows one embodiment 10 of a ubiquitous system having a high performance back-end processing server, such as a central control and processor 16. Processor 16 is used in conjunction with transducer devices, such as devices 21, which can move from room to room or from office to office as one or more physicians (101-104) moves about. Signals 13 to and from each device 21 are transmitted, for example, via antenna 22 (room 1) to trans/receiver 12-1 and to/from trans receiver 12-1 and server 16 via antenna 15 and transmission path 14-1. Transmission path 14-1 can be wireless or wireline or a combination thereof. Also, receiver (radio access point) 12-1 can serve a plurality of rooms or locations or could serve a particular room, as shown by (12-1, 12-2, 12-3, 12-01, 12-02).

The processing power of process 16 (which acts as a server) is designed to be capable of simultaneously processing data received from multiple radio access points. In return, if desired, processed signals, usually containing images are communicated back to the proper room for display. For example, display 23 in room 1 shows image 18-1 taken from the patient by Dr. 101 in room 1, while display 23 in room 3 shows image 18-3 taken by Dr. 102 in room 3. Similarly, Dr. 103 in office 1 can view images taken from office 1 via display 23 at office 1.

This operation may be accomplished by implementing multiple ASICs and multiplexing switches in parallel in server 16 which can be interfaced to an acquisition bus and to video bus as will be discussed. The bandwidth of these buses is designed to be broad enough to support the simultaneous processing of image data received from the various radios of multiple devices 21. The bandwidth also preferably supports sending data to multiple monitors 11 concurrently. Memory 17 operates in conjunction with server 16 to match data from a particular room with data flowing to that room and with other stored data as necessary.

The user interface for image controls is preferably easily accessible by the user to facilitate roaming between rooms. This can be done by making the transducer independent of the monitor as will be discussed with respect to FIGS. 2A and 2B.

Each radio access point (12-1, 12-2, 12-3, 12-01, 12-02) can be implemented by any radio having sufficient bandwidth. For example, a 7.5 GHz ultra wide band (UWB) radio band, spanning from 3.1 GHz to 10.6 GHz, broadband personal area network applications. This 7.5 GHz band contains 13 bands to support multi-user application as described in the 802.15.3 Ga proposal. Each UWB radio band could support a data rate of 110 Mb/sec at a range of 10 meters. There are also a total of 300 MHz in 12 bands available from 802.11a UNII band and three 22 MHz bands available for 802.11a and 802.11b ISM band. 802.11a, g, b are developed for wireless local are network applications. They cover more range than the UWB; however, they have lower data rates and consume more power. For short distance communication, UWB is specified to consume 100 MW for 110 Mbps rate at 10 meters whereas the WLAN 802.11a and 802.11.8 radios typically consume 1 to 2 watts and cover a range of 30-100 meters at 54 Mbps. Since the handheld scanhead is battery-powered, power consumption is an important design factor to the usability of handheld ultrasound. Technologies useful in providing power efficient and portable medical diagnostic equipment are shown and described in U.S. Pat. No. 5,722,412 dated Mar. 3, 1998 and U.S. Pat. No. 6,471,651 dated Oct. 29, 2003, each commonly assigned to the assignee of the present application, the disclosures of which are hereby incorporated herein by reference.

The recent release of third generation mobile services 3G provides much greater bandwidth to cellular handsets. The CDMA 1xEVDO allows a rate of 2.4 Mbps downlink and greater than 384 kbps uplink for data transfer. Availability of 3G enables E-mail, World Wide Web and other Internet based services through mobile handsets. However, the bandwidth of 3G radio is not yet broad enough for implementation of the radio access point to support the real-time imaging applications. 3G radio, however, could be found useful in a variety of tele-ultrasound applications based on the store-and-forward method discussed herein.

Let us now assume that UWB radio is chosen for implementation of radio access points, such as 12-1, in the wireless ultrasound network shown in FIG. 1. A single UWB radio access point may cover a range of 10 meters at a rate of 110 Mbps. Additional access points may be placed at different distances to ensure overlapped radio coverage of all scanning rooms of interest. In the embodiment shown, each room has a unique access point, but rooms can share access points. Physicians may scan patients in any room using a handheld ultrasound device 21. The device need not contain a monitor if a monitor 23 is also installed (or available) in that scanning room. Many physicians may scan patients in different rooms simultaneously by time-sharing back-end processor 16, assuming proper bandwidth is available in the wireless network.

Since the image file system is located centrally, all images are buffered in processor 16 and can easily be archived, for example in memory 17, or forwarded to various locations via communication(s) link 19, which could be the Internet or any other transmission system. The system of a preferred embodiment is always on and ready and thus a physician may start scanning a patient immediately after the handheld transducer's power is turned on and may do so in any scanning room. The physician may have access to medically relevant information available in the network, such as patient history, lab reports, pharmaceutical, insurance information and medical resources for assisting in making a diagnosis at the point-of-care. This information can be obtained via communication link 19 or from one or more memory 17.

Figure 2A:
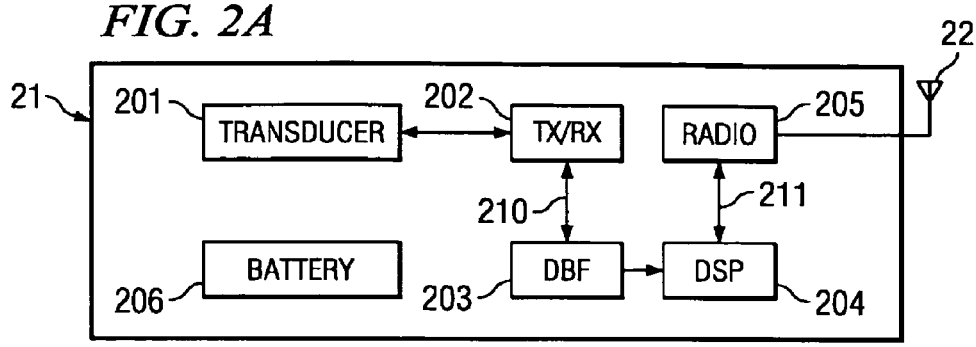
FIG. 2A shows a portable transducer device.

FIG. 2A shows one embodiment 21 of a handheld transducer containing imaging electronics integrated with transducer 201 inside a package approximately 6.5"×2.75"×1.25" in size. In the embodiment shown in FIG. 2A, the electronics are partitioned into four processing blocks; transmit/receive (Tx/Rx) 202, digital beam former (DBF) 203, digital signal processor (DSP) 204 and radio 205. Power is in the form of battery 206.

Pulser circuits, high voltage multiplexor circuits, low noise time gain control amplifiers are integrated into Tx/Rx 202. Multiple A/D converters, digital beamforming circuits and control logic are integrated in DBF 203. DSP 204 comprises circuits utilized for echo and flow signal processing and include analytic signal detection and compression, multi-rate filtering, and moving target detection capabilities. In a preferred embodiment, DBF 203, DSP 204 and BE 205 would be implemented using digital CMOS ASICS and mixed-signal technologies and Tx/Rx 202 would be implemented based on high-voltage and bipolar technology. The total weight of the scanhead module in one embodiment is 11.4 ounces. Excluding the housing, transducer 21, in one embodiment, weighs about 7.9 ounces. The peak power consumption is approximately 9.2 watts. Average power consumption with power management is approximately 5.15 watts.

Note that while a wireless transducer is shown, the transducer could be hardwired to the common processor or to a relay point and then the communication could be wireless to the processor.

Figure 2B:
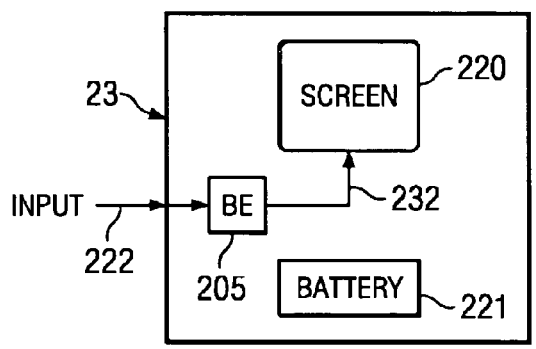
FIG. 2B shows a monitor.

FIG. 2B shows display 23 having screen 220 for display of data including image data, a power source, such as battery 221, and input 222 for receipt of data to be displayed. Input 222 can be hard wired or a wireless input or a combination of both. The input can come from the output of device 21, for example from antenna 22, or from processor 16 (FIG. 1). When data comes from device 21, BE 205 is preferably provided for processing the data for proper display. Image processing, scan conversion and video processing are implemented in BE 205, which supports many image manipulation functions. In addition, a general purpose embedded microprocessor may be integrated in BE 205 for user interface control, image analysis and measurement. According to embodiments, when the data comes from processor 16, the "backend" processing is accomplished in processor 16 and need not be repeated at display 23.

For video streaming, a substantial amount of data bandwidth is needed and it has been found that the bandwidth required for transmitting the "un-compressed" color VGA video in real time may exceed 200 Mbps. Video stream techniques are now well-known and can be employed in this system.

In order to integrate wireless technology and ultrasound, one important task is to analyze the required data rates at different stages in the ultrasound image formation process to determine a system partition so that the available radio bandwidth may be most efficiently utilized. Such a determination according to one embodiment begins with an examination of data rates required for acquiring a sequence of ultrasound image frames at three different bus locations with respect to transducer 21, as shown in FIG. 2A. These locations are RF bus 210, acquisition bus 211 and video bus 232 (FIG. 2B.)

RF bus 210: Significant radio bandwidth is required over link 210. For example, if the beamformed RF signals from transducer 201 are sampled at 20 MHz and digitized into 16 bits, then the required data transfer rate may exceed 320 Mbps. Currently (UWB) appears to be the only broadband radio link that supports this rate. However, the covering range for UWB radio at this rate is only about 4 meters.

Acquisition bus 211: Only moderate radio bandwidth is required at link 211. Thus, since the beamformed RF signal is filtered, decimated and detected in DSP processor 204, the bandwidth is greatly reduced at this point. For example, assuming there are 128×512 pixels in one image frame and eight bits per pixel, to transmit 30 frames/sec of image data prior to scan conversion, the data rate is about 16 Mbps. This is about a factor of ten reduction in data rate as compared to that at link 210.

Video bus 232: the data rate increases again at link 232 (FIG. 2B) after the image lines are scanconverted into video frames. The data rate may reach 85,221 Mbps depending upon the color image frame format. Clearly, partitioning the system at link 211 requires the least overall bandwidth for interconnection between transducer 21 and video processing.

Establishing a point-to-point communication from device 21 using partitioning at link 211 sets up a basic imaging system with a single transducer. More than one scanhead may simultaneously access central processor 16 (or display 23) provided that the radio bandwidth and processing power for backend process are available.

Returning for a moment to FIG. 1. It has been discussed that readings using an ultrasound device or from any other type of device and taken from different rooms or from different offices can be transmitted either directly or through an intermediary transport system to central control processor 16. Central control and processor 16 can then perform analysis image enhancement and any other type of processing required. This processing could, for example, include comparing the presently obtained data to previously obtained data from memory 17 or from an external source via the internet or otherwise. This data then can be sent back, either hard wired or wireless via path 19 or via the transmission path from antenna 15 to the appropriate display 23 in the room in which the data is being taken from the patient. Thus, data from room 1 would of course would be returned to display 23 in room 1, while data from office 2 would be returned to display 23 in office 2. The data, as its being obtained and sent from a location, can be tagged so that processor 16 knows from where the data is coming and to where it is to be returned. At the same time, or at a different time, the data that is brought into processor 16 from the various different offices and rooms can also be transmitted to different experts, either in the same facility or remotely anywhere in the world. This transmission could be, for example, via output 19 which can be the internet, wireless, or wireline transmission.

Figure 3:
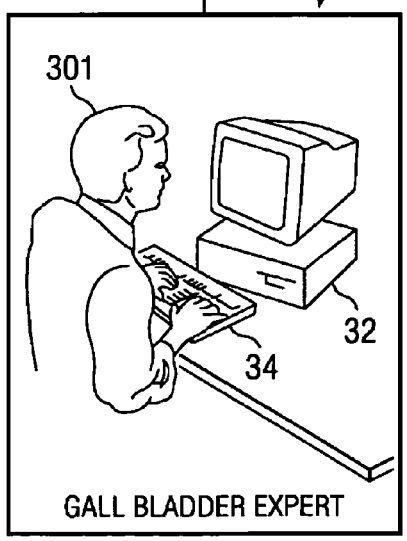
FIGS. 3 and 4 show diagnostics performed remotely by different specialist.

For example, assume that a sonogram of a gall bladder is being taken from a patient in, for example, room 2 of FIG. 1. This information could be received by processor 16 analyzed therein and transmitted to gall bladder expert 301 at location 30, as shown in FIG. 3. The gall bladder expert, using equipment in his or her office, would then review the data, compare it to other data, and send back analysis and even a treatment course, if desired. This can all be done in real time, if desired. Expert 301 may use keyboard 34, and computer 32.

If for example, the sonogram or any other instrument were being used by a physician say in office 1 to look at the heart of a patient, then processor 16 could determine that this is a heart issue and send the information to heart expert 401 at location 40 and the heart expert then could respond as discussed above.

FIG. 5 shows one embodiment of flow chart 50 for controlling the ubiquitous system. This control could occur via processor 16. Process 501 determines if a new signal is arriving from a patient. If its not a new signal, processing continues via process 510. If it is a new signal process 502 determines the identity of the sending unit, or process 503 determines the identity and location of the patient. This information can be provided by keyboard, spoken message or otherwise from an examining attendant with respect to the patient.

Process 504 determines, if desired, the signal type, i.e. whether it is sound, MRI, Xray, etc. that is being received. Process 505, if desired, determines the image area, i.e. heart, kidney, gall bladder, thyroid, etc. This determination can be made either by the attending physician or by spoken word, key input or by processor 16 analyzing the data to determine what area is being scanned.

The signal is then processed by process 510 as discussed above with respect to backend processing and additional processing can be utilized, if desired.

Process 511 performs diagnostic operations on the data and could also optionally retrieve previous records, normal records for comparison, or any other type of records. Process 512 determines whether to send the signal to the patient's room and if that option is selected then the signal is sent to display 23 in the patient's room for real time viewing by the attending physician.

Process 513 is an optional process to determine if the signal should be sent to an expert. If it should be sent to an expert then the proper expert is selected. This selection can be done automatically by signal comparison or otherwise or by a code that is selected by the attending physician. Process 516 and process 517 selects and sends the signal to the specialty expert.

Figure 4:
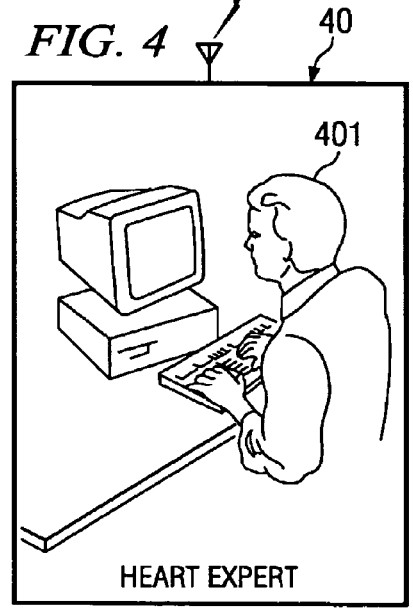

The specialty expert was discussed with respect to FIGS. 3 and 4 and many such experts can be available and utilized across different areas or within a single area. Process 515 is utilized when a single expert is utilized for different types of signals and the expert can further direct the signal or diagnose the situation in real time him or herself.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed is:

1. A method of examining a patient comprising:

positioning a transducer with respect to a patient so as to obtain electronic signals from selected locations of said patient; said signals capable of analyzation for diagnostic purposes;

transmitting obtained ones of said electronic signals to a processor, said processor arranged to receive electronic signals from transducers located at a plurality of different locations;

transmitting from said processor to a location of a transducer image data processed by said processor, said processor data for displaying images based on real-time obtained data from said transducer at said location;

transmitting to a third party at least a portion of said data received from a transducer at a particular location;

transmitting data from said third party to said particular location of said transducer, wherein said last-mentioned transmitted data comprises information from said third party useful for medical treatment of said patient at said particular location.

2. A medical system comprising:

a plurality of wireless ultrasound transducers;

a processor common to said plurality of transducers;

a plurality of short range relay units for obtaining wireless signals for said transducers and for transmitting said signals to said common processor;

a display in locations where said ultrasound transducer can be used for obtaining diagnostic signals from a patient; and a transmission link from said common processor to each said display for sending to a display at a location where said transducer is being used to obtain diagnostic signals, processed images of said diagnostic signals obtained at said location;

a link from said common processor to a third party expert; said link operable for sending at least a portion of data from a plurality of locations to said third party; and a link from said third party selectively to a display associated with a transducer from which said data was obtained, said link operable for providing medically relevant data to said display pertaining to said data obtained at said associated transducer.

3. The system of claim 2 wherein said links are temporarily established for the duration of a data transfer.

* * * * *